United States Patent [19]

Levy

[11] 4,026,304
[45] May 31, 1977

[54] BONE GENERATING METHOD AND DEVICE

[75] Inventor: Didya D. Levy, Brooklyn, N.Y.

[73] Assignee: Hydro Med Sciences Inc., New York, N.Y.

[22] Filed: Nov. 6, 1974

[21] Appl. No.: 521,407

Related U.S. Application Data

[63] Continuation of Ser. No. 243,207, April 12, 1972, abandoned.

[52] U.S. Cl. .................... 128/419 F; 3/1; 128/82.1; 128/422
[51] Int. Cl.² ............................. A61N 1/36
[58] Field of Search ........... 128/1 R, 82.1, 92 C, 128/92 CA, 419 F, 419 PG, 419 R, 421, 422; 3/1

[56] References Cited

UNITED STATES PATENTS

| | | | |
|---|---|---|---|
| 2,936,762 | 5/1960 | Bernard | 128/422 |
| 3,357,434 | 12/1967 | Abell | 128/419 PG |
| 3,474,353 | 10/1969 | Keller, Jr. | 128/422 |
| 3,543,761 | 12/1970 | Bradley | 128/421 |
| 3,605,123 | 9/1971 | Hahn | 128/92 C |
| 3,745,995 | 7/1973 | Kraus | 128/419 F |

Primary Examiner—William E. Kamm

Attorney, Agent, or Firm—Cushman, Darby & Cushman

[57] ABSTRACT

A method and apparatus for stimulating in vivo bone growth whereby a train of electrical pulses, rather than a direct current potential, is applied to the bone in vivo to produce faster and more satisfactory growth than a direct current voltage. In the embodiment described below, an astable multivibrator producing a pulse train with a duty cycle preferably between 1/10% and 10% is encapsulated in a corrosion resistant material which is, in turn, coated with a non-toxic, non-tissue reactive coating to produce a self-contained prosthetic which will stimulate bone growth.

A second component of this prosthetic system is comprised of a suitable substrate material that can be electrically driven to induce tissue infiltration into the substrate pore structure. This second component of the prosthetic system is not required for the proper functioning of the active component of said prosthetic system but may be used as an adjunct aid if the attending physician so elects. In the embodiment described below, several classes of such materials are discussed. These materials are non-toxic and non-tissue reactive and are of such design as to readily permit tissue infiltration.

23 Claims, 4 Drawing Figures

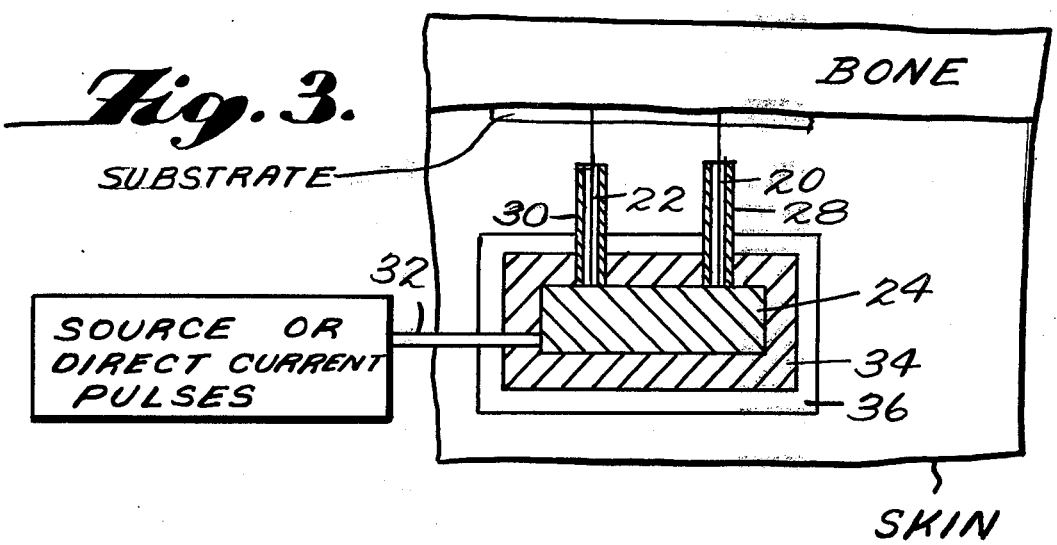
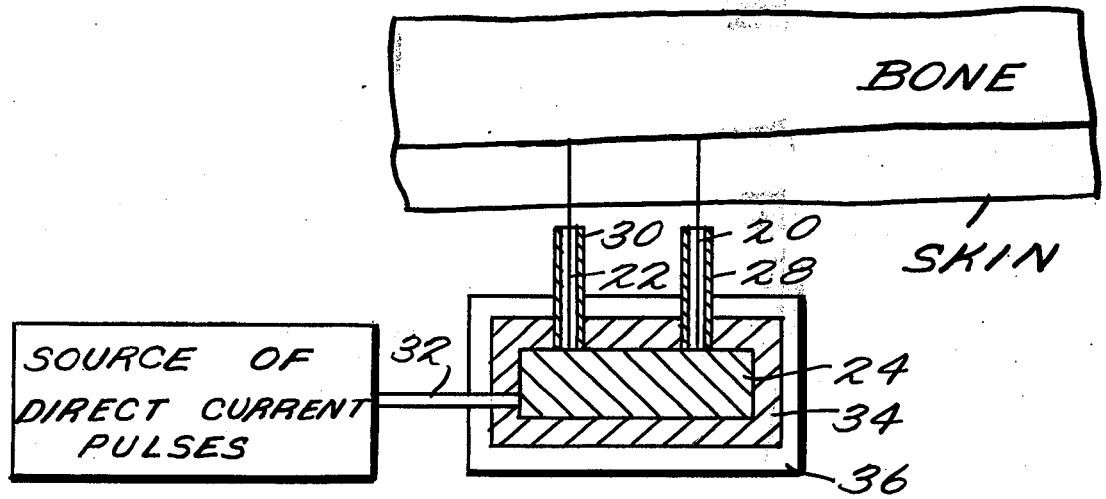

BONE GENERATING METHOD AND DEVICE

This is a continuation, filed Apr. 12, 1972 and now abandoned.

INTRODUCTION

The invention relates to a method and apparatus for stimulating in vivo bone growth.

This invention and its implications are further described in a Doctoral Dissertation by the inventor entitled "Induced Osteogenesis by Electrical Stimulation" available at the Polytechnic Institute of Brooklyn and an article of the same title by the inventor which appeared in The Journal of the Electrochemical Society, Volume 118, No. 9, September 1971. The disclosures of these references are hereby explicitly incorporated herein by reference.

One of the remarkable things about bone, in addition to its ability to mend itself when broken, is its ability to alter gross geometry in response to an externally applied load in such a way that the applied stress is lessened and possibility even minimized. This phenomenon is known as remodeling and was first noted by Wolff in 1892. As with all reference to individuals below, the citation to the published work can be found in the above mentioned dissertation. The mechanism by which this occurs is not known. In 1957 two Japanese workers, E. Fukada and I. Yasuda, suggested that bone behaved as a piezoelectric crystal. This conclusion was tantamount to identifying a transducing element of bone that would permit communication between an externally applied mechanical load and some element on a biological level that would respond to this stimulus. This observation was later independently confirmed by two groups working in the United States; one in 1962 headed by C. A. L. Bassett at the Columbia University College of Physicians and Surgeons, and the second in 1963 headed by M. H. Shamos and L. S. Lavine at the Downstate Medical Center.

In 1964, the group headed by Bassett published a series of curves purporting to show the voltage response of bone to a step deformation. These curves, and others like them published by Cochran, Steinberg, and Gillooly, form the mathematical basis for analyzing the transducing mechanism alluded to above. In effect, these curves permit bone to be treated as a black box system and, as such, analysis of the system temporarily moves from a biological to an analytical domain. Without directly stating this, Becker implied this in a 1966 paper when he attempted to qualitatively identify some of the necessary block elements of a dynamic model of the bone remodeling system. According to this model, an external stimulus should be able to evoke a cellular response, and this response, in turn, would be able to mediate the stimulus in such a way as to diminish its effect. The stimulus for this negative feedback system is an externally applied load which causes a local deformation of bone. The remodeling system then responds by a series of changes to the bone structure which presumably alters bone geometry in such a way as to best resist the deforming load. To affect this series of changes, though, several transducing mechanisms must be activated. One of these transducers must serve to translate the local deformation into something recognizable on a cellular level. It is this transducer that Cochran, Steinberg, and Gillooly have identified while measuring the variation in surface potential of a cortical strip subject to a known bending stress. These surface potentials presumably exist in vivo and are presumed to trigger the remodeling system to respond in a specific fashion.

If this scheme is correct, then several things should follow. It should be possible to quantitatively characterize the transducing mechanism, i.e., to identify its transfer function. It should be possible to build a stimulator that capitalizes on this information, and to incorporate this stimulator into an in vivo system and permit it to trigger the remodeling system just as the actual transducer does. Several attempts have been made to induce bone growth by electrical techniques.

One of the first attempts to initiate bone growth by electrical stimulation was reported by Yasuda and Noguchi in 1955. They used a voltage source consisting of a 1.5 volt battery in series with a resistor. They report delivering a constant DC current of 1 $\mu$a for 3 weeks. It is assumed that the 1 $\mu$a figure is for the unloaded circuit since no mention is made of monitoring the battery pack in vivo. No mention is made of the encapsulating material nor of the type of electrodes used. They further reported that when current levels were between 1 $\mu$a and 100 $\mu$a, a bony callus formed extending through the periosteum from "pole to pole."

The claim was made by these two investigators that more callus was formed near the cathode than the anode. Yet no photos were presented to substantiate either claim. They also reported that if current levels exceeded 100 $\mu$a, a cartilagenous callus formed and if current levels exceeded 1 ma bone destruction ensued. It is important to note that these figures for so-called current levels probably occurred only in the unloaded battery packs, that the authors were in all likelihood unaware of the amount of electrode polarization, that the local impedance seen by these electrodes would determine the actual current output of these devices, and that this output would vary as the local impedance varied.

In 1964 Bassett, Pawluk, and Becker reported a similar experiment. The battery packs they used consisted of a 1.4v battery in series with various resistors so that the current through these resistors was 1 $\mu$a, 10 $\mu$a, and 100 $\mu$a when the circuit was unloaded. The electrodes were platinum-iridium and the devices were encapsulated first in epoxy and then coated with silicon rubber. Current was not monitored in vivo and so the authors had no firm idea of what the operating characteristics of these devices were. Current was, however, monitored in situ for a 30 minutes period during which time it was noted that both the 10 $\mu$a and 100 $\mu$a battery packs stabilized their output near 3 $\mu$a and 1 $\mu$a pack near ½ $\mu$a. They qualitatively reported bone formation about all active and control electrodes with more bone forming near the active cathode than near the active anode. This new bone was characterized as non-oriented, young trabecular bone and the substantiating photomicrographs were presented.

The use of microcurrents to induce growth seemed to indicate a system with a very low threshold sensitivity and so an attempt was made to trigger growth using the current generated by the reduction of a bimetallic wire strip. Smith used a silver-platinum wire embedded in the limb of a frog after a portion of it had first been amputated. The Pt-Ag couple produced a voltage drop of 0.2v in Ringer's solution and presumably something close to this in the forearm of the frog. He reports that simple amputations resulted in partial limb regeneration with a frequency of 13%, a partial regeneration frequency of 13% when a plain silver strip was implanted, and a partial regeneration frequency of 87% when a bimetallic strip was implanted.

Three years later, in 1970, Wilson performed a similar series of experiments using a plain braided copper-constantan wire electrode to induce longitudinal growth in the tibia and femurs of adult rabbits. With a plain copper or plain constantan braided electrode as a control, and the untouched contralateral limb as a base, he reported overall increases in length of about 2% with the control electrodes and slightly over 3% using the test electrodes. Somewhat more growth occurred when a heavier gage electrode was used but the increase in growth could not be correlated with increases in the mass of the electrode. Longitudinal growth was sometimes accompanied by a thickening of the cortex and the filling up of the medullary cavity with cancellous bone. Wilson encountered no success when he attempted to induce growth by electrical stimulation primarily because of mechanical breakdowns.

Minkin in 1968 attempted to induce growth across the epiphyseal plate. Two holes were drilled on either side of the epiphyseal plate of the distal femur and a DC device capable of delivering 70 $\mu a$ when unloaded was implanted with the cathode in the metaphysis and anode in the epiphysis. A passive control was used in the contralateral bone. Parameters for measuring change included gross deformities, physical dimensions, width of metaphysis, and a composition analysis. The author then simply noted bony growth both at the active cathode and to a lesser extent, in the control femur.

The same year Friedenberg attempted to influence the growth of bones in immature rabbits. His stimulator was a DC voltage source powered by a 1.4v battery in series with one of a number of resistors ranging in value from 33 ohms to 39 kilohms. Teflon coated stainless steel electrodes were implanted in the epiphysis and the metaphysis. Current was monitored in vivo with a microammeter. Current levels, electrode placement, and experiment duration were varied and the appropriate tissue response was then noted. Results show no significant growth of the shaft and a high incidence of bone destruction near the positive pole when it was implanted in the epiphysis. Further, there was minimal formation of new bone trabeculae or cartilage nodules arising in the "rim of vascular granulation tissue surrounding the negative electrode." No increase in vascularity was noted near the negative electrode.

The following year Yarington made the observation that augmentation of the negative DC potential associated with normal tissue regeneration might accelerate the reparative process. Accordingly, he employed battery packs presumably operating at a constant DC current of 2-3 $\mu a$ for 14 days. He notes growth at the negative pole and resorption at the positive pole. He further reports a direct effect on osteoblastic mitosis in the vicinity of the negative pole which is lost if higher current levels are used.

Thereafter, O'Connor attempted to take advantage of the observation made by Bassett's group reported above, viz., that a massive amount of endosteal bone formed around the cathode, and accelerate the fracture healing of rabbit metacarpals using a technique similar to theirs. He reported no results comparable to those claimed by Bassett. However, when O'Connor repeated Bassett's experiment rather than his own variation of them, he did come to the same general conclusion arrived at earlier by Bassett. O'Connor observed that the type of bone that formed around electrically active electrodes was nearly identical to that formed on control electrodes; only the amount varied and the cathode did not always have the most bone surrounding it.

In two papers published in 1969, Lavine attempted to standardize in some fashion those attempts made to demonstrate bone growth by electrical stimulation. His statement was that the variability in reported results, as indicated above, was due to a number of factors including foreign body reactions (electrode insertion), local heating effects, and unmonitored variations in current. Lavine's proposed solution involved the use of a cortical defect situated between the two drilled holes in which the platinum electrodes of a battery pack were placed. At that time the observation was made that newly forming bone was always anchored to preexisting bone. In Lavine's experiment, which lasted 2-3 weeks, DC current was monitored by a microammeter. The claim was then made that each of the three objections listed above had been circumvented and that in addition the healing process within the defect was "markedly enhanced."

The problems associated with all of these attempts to stimulate bone growth with a DC voltage source are severalfold. Among them is the fact that there is little mathematicial justification for stimulating the system with a DC voltage source. A second problem is that as local impedance changes occur in tissue structures surrounding the electrodes, the amount of current passing through the bone will vary. Both of these difficulties have led to a common observation among investigators that the response to DC voltage stimulation is marginal and not always apparent.

The invention described herein obviates the major difficulties experienced by other investigators and, as such, represents a radical departure from other attempts to stimulate bone growth. The present invention is founded on a mathematical model with a strong quantitative basis, and circumvents difficulties associated with DC electrode polarization by using a wave form with a short duty cycle. The peak output circuit of the invention can be controlled independent of variation in local tissue electrical impedance. The response of bone to the type of stimulation generated by the invention is reproducible. This response is characterized by increases in bone volume in the vicinity of stimulation of upwards of 50% after 2 – 3 weeks of stimulation and will be further described in the examples that follow below.

SUMMARY OF THE INVENTION

The invention of this application relates to a novel method and apparatus wherein a train of electrical pulses rather than a constant direct current voltage is applied to the bone. As is apparent from the results described in detail below, the improvement in bone growth using this system as compared to constant direct current stimulation is striking.

In the specific embodiment described in detail below, an astable multivibrator circuit is encapsulated in a corrosion resistant material which is, in turn, coated with a non-toxic, non-tissue reactive coating and then implanted near the bone to be stimulated. A pair of insulated electrodes extend through the coating and encapsulating material to the astable circuit for applying the pulse train to the bone. The pulse train preferably has a duty cycle between 1/10% and 10% and a firing rate between 0.01 Hz and 10KHz, preferably between 0.01 Hz and 1KHz.

Further, the invention of this application contains a second element comprising a non-toxic, non-tissue reactive substrate of a material or materials as described below. Hydrophilic material is preferable, but not required. Such materials can serve as a mechanical substrate into which newly formed, rapidly generated, viable bone can infiltrate and attach when said mechanical substrate is activated by the electrical element of this invention. Active bone stimulation does not necessarily require the presence of a passive substrate and, at the election of the attending physician, the passive element may be omitted from an indicated application. Alternatively, the attending physician may exercise an option for the use of said passive element coincident with the indicated surgical procedure and patient pathology.

BRIEF DESCRIPTION OF THE DRAWINGS

FIG. 3 shows the implant unit implanted next to a bone and beneath the skin.

FIG. 4 shows the implant unit positioned exteriorly of the skin with the electrodes in contact with the bone.

Referring now to FIG. 1, a battery, shown as $V_{input}$ is connected respectively to transistors $T_1$ and $T_2$. A capacitor C is connected across the base of transistor $T_1$ and the collector of transistor $T_2$ while a timing resistor, $R_T$, is also connected to the base of transistor $T_1$ and the positive terminal of the battery.

A load resistor $R_L$ is connected across the collector of transistor $T_2$ and the emitter of transistor $T_1$ while a small dropping resistor $R_I$ is connected to the low potential side of the load resistor $R_L$. The direct current pulses $V_{out}$ will be generated as follows. The transistor $T_2$ is normally in a non-conducting condition and acts as a switch which is normally in an open condition. As the pulse is formed, the transistor $T_2$ is changed into a conductive condition which effectively closes the switch in the circuit and supplies a voltage drop across the loader resistor $R_L$. The pulse repetition rate is set by the capacitor (C) resistor ($R_T$) which together effectively form a conventional RC timing circuit.

Transistor $T_1$ is also normally in a non-conducting condition. As power is applied to the circuit from the battery, capacitor C will begin to be charged and a small current begins to pass through the load resistor $R_6$. The voltage across resistor $R_L$ will continue to enhance the current in the circuit charging the capacitor C and will act as a positive feedback until the transistor $T_2$ is saturated or caused to change into a conductive condition. The actual pulse duration will only be as long as sufficient current flows through the capacitor C in order to keep the transistor $T_2$ in a saturated condition. Thus, when transistor $T_2$ becomes unsaturated a negative feedback will rapidly turn off transistor $T_2$ and the pulse will be completed and the timng circuit will initiate the beginning of the next pulse.

Figure 1:
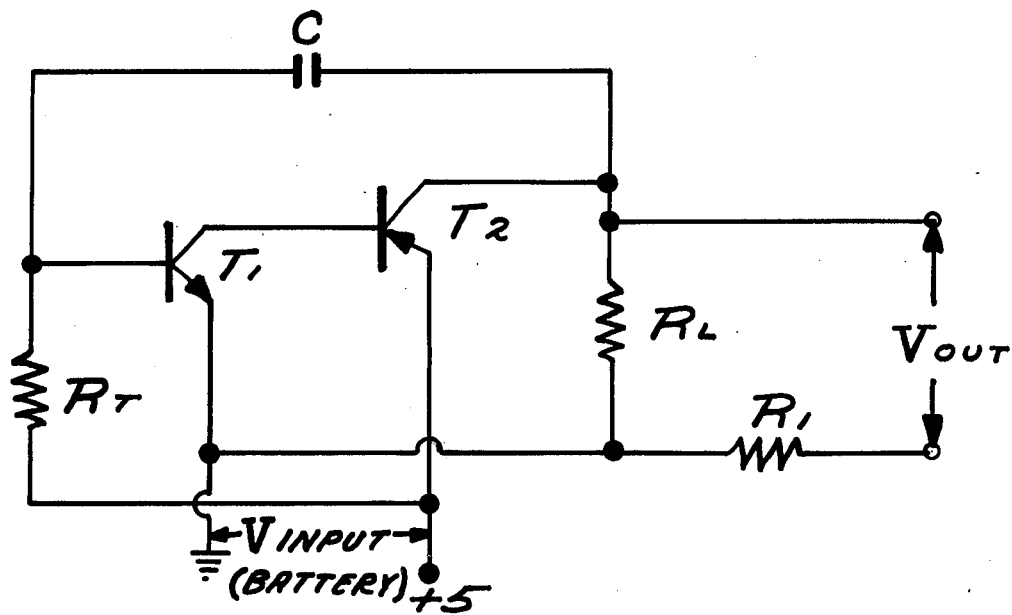
FIG. 1 shows an electrical schematic of one possible circuit for producing a pulse train to stimulate in vivo bone growth.
Figure 2:
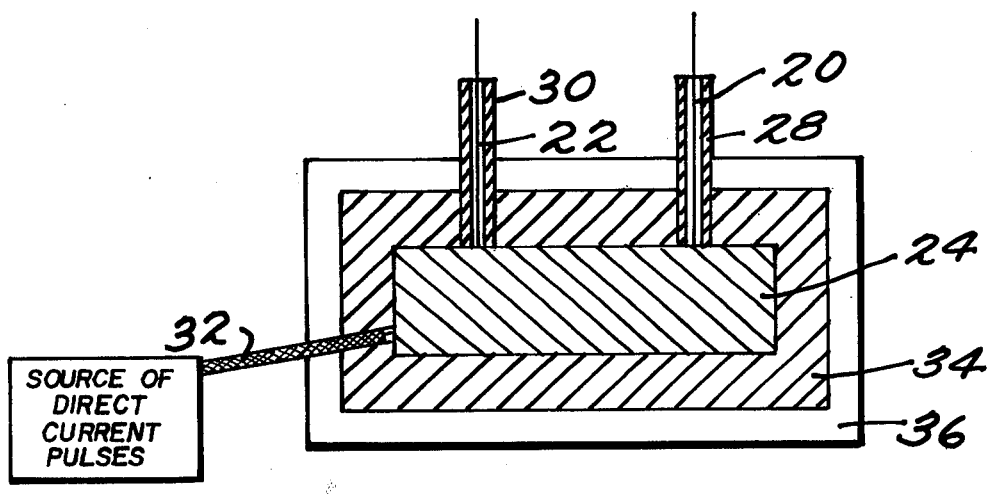
FIG. 2 shows a cut-away view of one of many designed implantable units incorporating a circuit such as shown in FIG. 1.

Reference is now made to FIG. 2 which shows a prosthetic device suitable for implantation which incorporates a small encapsulated electrical oscillator circuit such as shown in FIG. 1 whose output characteristics (pulse waveform, firing rate, and peak output current) can be fixed or varied prior to use. As discussed above, the oscillator depicted in FIG. 1 may, at the option of the investigator, be manufactured with electrical taps to monitor in vivo operating characteristics. This electronic system can be constructed of current state-of-the-art-micro-transistors, resistors, capacitors, and batteries or modified integrated circuit chips using conventional spot welding or soldering techniques.

A pair of driving electrodes 20 and 22 extend from the circuit 24 for applying the output pulses to a bone. The electrodes are preferably mechanically strengthened against the surrounding environment by enclosure in suitably rigid sleeves 28 and 30. Electrodes 20 and 22 can be fabricated from stranded stainless steel (type 316) wire, stranded silver wire, pure silver wire, platinum-iridium wire (30/70 Pt-Ir, 10/90 Pt-Ir), or pure platinum wire suitably insulated by a biologically inert material such as medical grade teflon. The output monitoring cable 32 can be constructed of similar materials.

The electrode and cable materials mentioned in this example are representative of many possible electrode and cable materials and are not intended as a limitation of the invention. The electrode configuration may assume any of a number of possible electrode designs. Among these possible electrode configurations are those constructed of a conducting monofilament or multifilament insulated up to its tip but not including insulation of the cross-sectional area at the tip, conducting monofilaments or multifilaments of various lengths that are partially insulated depending upon the amount of tissue the attending physician wishes to be stimulated, and conducting films, meshwork arrays, or plates of different geometrical configurations that vary with the application decided upon by the attending physician. Some of the possible applications and electrode configurations are discussed in the examples that follow.

Circuit 24 is preferably encapsulated in a corrosion resistant material forming an inner layer 34. Materials which can be used to encapsulate the electrical circuit and protect it against the corrosive effects of the biological environment include the arcylics such as poly(-butyl acrylate), poly(methyl methacrylate), poly(ethyl methacrylate), poly(n-butyl methacrylate), epoxy resins, polyesters such as Goodyear "Vitel Resin PE100-X", cellulose derivatives such as cellulose acetate, ethyl cellulose, polyamides such as nylon (type 6/6), Versamide-100, 115, 900, -930, -940, styrene polymers and copolymers, poly (vinyl chloride) and copolymers, poly (vinyl butyl ether), Elvax 250, fluoroplastics such as polytetrafluoroethylene (TFE), Fluorinated ethylene propylene copolymer (FEP), polyethylene, polypropylene, ethylenepropylene-diene terpolymers, Lexan-100 a polycarbonate resin, and the medical grade silicone resins. These encapsulating materials are only a few of many possible encapsulating materials. No limitation of the invention to these particular encapsulating materials is intended.

A layer 36 of a non-toxic, non-tissue reactive coating e.g., of Hydron(2-hydroxyethyl methacrylate polymer) is preferably placed over encapsulation layer 34. The most preferred coatings are non-toxic, non-tissue reactive, and biocompatible. Typical examples of these coatings are those prepared from the following polymerized monomers: A hydrophilic monomer which is a hydroxy lower alkyl acrylate or methacrylate, or hydroxy lower alkoxy lower alkyl acrylate or methacrylate, e.g., 2-hydroxyethyl acrylate, 2-hydroxyethyl methacrylate, diethylene glycol monoacrylate, diethylene glycol monomethacrylate, 2-hydroxypropyl acrylate, 2-hydroxypropyl methacrylate, 3-hydroxypropyl acrylate, 3-hydroxypropyl methacrylate and dipropylene glycol monomethacrylate. The preferred monomers for preparing these polymers are hydroxyalkyl acrylates and methacrylates, most preferably, 2-hydroxyethyl methacrylates. The polymers produced from said monomers are organic solvent soluble, e.g. alcohol soluble, but water insoluble. They can be prepared for example as shown in Shepherd U.S. Pat. No. 3,618,213 e.g. example 36a, or Chromacek U.S. Pat. No. 3,575,946.

The hydroxyalkyl acrylate or methacrylate less preferably can also be replaced in part by vinyl pyrrolidone, acrylamide, methacrylamide, N-propyl acrylamide, N-isopropyl methacrylamide, N-methylacrylamide, N-methylmethacrylamide, N-methylol acrylamide and N-methylol methacrylamide, N-2-hydroxyethyl acrylamide, N-2-hydroxyethyl methacrylamide. However, these monomers usually form water soluble homopolymers and hence they require the presence of a cross-linking agent or copolymerization with a sufficient amount of the hydroxyalkyl acrylates and methacrylates to render the copolymers water insoluble.

Other ethylenically unsaturated monomers can be used in conjunction with the above monomers to constitute hydrophilic polymeric matrixes. They include neutral monomers such as acrylonitrile, methacrylonitrile, vinyl acetate, alkyl acrylates, methacrylates, alkoxyalkyl acrylates and methacrylates. Other vinyl monomers bearing ionizable functional groups can be copolymerized with the hydroxyalkyl acrylates or methacrylates.

Examples of alkyl acrylates and methacrylates include methyl acrylate, ethyl acrylate, butyl acrylate, 2-ethylhexyl acrylate, methyl methacrylate and butyl methacrylates. Examples of suitable alkoxyalkyl acrylates and methacrylates are methoxyethyl acrylate, methoxyethyl methacrylate, ethoxyethyl acrylate, ethoxyethyl methacrylate, propoxyethyl acrylate, butoxyethyl methacrylate, methoxypropyl acrylate, ethoxypropyl methacrylate, these monomers used in an amount preferably not higher than 50 percent (and usually between 0.5 and 20%) of the monomeric mixture. Other vinyl monomers bearing ionizable functional groups can be copolymerized with the hydroxyalkyl acrylates or methacrylates. They include acidic type monomers such as acrylic acid, methacrylic acid, maleic acid, fumaric acid and itaconic acid. These acidic moieties are only a few of many possible ethylenically unsaturated acidic moieties which can be used. No limitation of the invention to these particular monomers is intended. They also include basic type monomers such as aminoethyl methacrylate, dimethyl aminoethyl methacrylate, monomethyl-aminoethyl methacrylate, t-butylaminoethyl methacrylate, p-aminostyrene, o-aminostyrene, 2-amino-4-vinyltoluene, diethylaminoethyl acrylate, dimethylaminoethyl acrylate, and t-butylaminoethyl acrylate. These basic moieties are only a few of the many possible ethylenically unsaturated basic moieties which can be used. No limitation of the invention to these particular monomers is intended. These ionegenic monomers should not be used in sufficient amounts to render the hydroxyalkyl acrylates or methacrylates water soluble. Other less applicable coatings include the medical grade silastics (rubbery polydimethyl siloxane) and silicone rubber, medical grade polyurethanes, and the medical grades of beeswax (Fisher Chemical W-24) and paraffin (Fisher Chemical P-19).

Frequently the polymer is sparingly cross-linked. The cross-linking agent can be added in an amount of 0.05% to 20% usually not over 2.0%.

Typical examples of cross-linking agents include ethylene glycol diacrylate, ethylene glycol dimethacrylate, 1,4-butylene dimethacrylate, diethylene glycol dimethacrylate, propylene glycol dimethacrylate, diethylene glycol dimethacrylate, dipropylene glycol dimethacrylate, divinyl benzene and ammonium dichromate.

A second substituent of this prosthetic system is an artificial polymeric matrix that can serve as a substrate alternative to pre-existing bone into which newly generated viable bone can infiltrate and attach. Typical of these matrixes are classes of foams such as poly (2-hydroxyethyl methacrylate) foam, expandable ABS (Acrylonitrile, butadiene, styrene terpolymer), expandable polypropylene, expandable vinyl, e.g. expandable polyvinyl chloride, polyurethance foams, cross-linked polyvinyl chloride foams, ethylene-propylene copolymer foams, ionomer foams, expandable polyvinyl alcohol foams (e.g., Ivalon), and silicone foams.

Further examples of classes of possible substrate materials include forms of elemental carbon, porous metal matrixes such as porous Vitallium, porous pure titanium and titanium-aluminum-vanadium alloys, oxides of titanium and aluminum in combination with calcium oxide (e.g. $TiO_2.CaO$ and $Al_2O_3.CaO$), ceramicepoxy composites (e.g., Cerosium), and ceramic-glass composites (e.g., those formed from a $SiO_2$-$P_2O_5$-CaO-$NA_2O$ system). These materials are intended as examples of possible substrate materials and no limitation of the invention is intended.

The primary constraint on these substrate materials involves internal pore size and design. In order that bone grow into the porous structure of the matrix, the pores must be sufficiently large to accommodate the organic and inorganic substituents of bone, bone cells of varying size, and blood vessel infiltration. The desirability of vascularization of the substrate complex compels the design of a matrix with sufficient pore interconnections as to permit ingrown vessels to freely anastamose with one another. Adequate vascularization of the substrate is extremely important for supplying both nourishment to the ingrown tissue and calcium and phosphate for the mineralization of the organic matrix.

The primary advantage of using this substrate component in connection with the electrically active portion of said prosthetic system lies primarily with the speed with which tissue infiltration can occure. In a typical passive ceramic complex (cerosium) implant, minute blood vessel infiltration is noted in 20 days in substrate implants driven electrically and will be reported in the examples that follow. The advantage of a significant reduction in the time required for tissue to infiltrate the substrate coupled with the ability to mold the substrate into a variety of shapes comprises a powerful orthopedic tool.

A representative example of the total system application utilizing both the active and passive components is the introduction of an artificial hip prosthesis, made of a suitable substrate material as outlined above, into the central lumen of the underlying femur. Active stimulation of the substrate-femur interface will accelerate the ossification of this juncture and create a structurally viable union.

Surgical constraints imposed on a given orthopedic prosthetic system by size and reliability considerations are met and surpassed by said invention. The active component of said invention, being fabricated of micro-miniature circuit components, can be made as small as is necessary for use on such patients whose tissue structure adjacent to the point of prosthesis application will not accomodate a device larger than a given size. As an example, the device can be manufactured small enough to attach directly to the long bones of laboratory rabbits without interfering with their normal activity. Alternatively, said invention as embodied in this text, need not be implanted adjacent to a surgical target or indeed within the subject but is flexible enough in its mode of operation to function extracorporally and deliver a prescribed signal along said electrodes as they extend from the signal source through the patient's skin to the surgical target.

The operating lifetime of said device is variable depending upon the mode used to supply power to the basic electronic circuitry. The mode most commonly envisioned by the text involved a fixed battery source whereby the operating lifetime is in excess of three months depending upon the number of battery sources used, as will be illustrated in the examples that follow. A slight modification of the power supply to include the use of commercially available rechargeable nickel-cadmium batteries (e.g., Eveready B-50) can extend the operating lifetime of said device for as long as is considered necessary by the attending physician. Remarks made herein regarding two forms of battery power supply, viz., fixed and rechargeable, are primarily directed towards circuits that are to be implanted subcutaneously. Should the physician elect to use a device that will remain extracorporal, said device can be supplied with power from battery sources that can be easily snapped into place.

The alternative mode of supply power to said device involves the use of an RF carrier to broadcast energy to an appropriate receiver contained within the circuit. The transmitter for such a system would be located on the person of the patient, and would supply energy through intervening layers of tissue to the receiver without injuring this tissue. The effective broadcast range of this transmitter would be a few feet at most and would not constitute a hazard to existing communication systems. An operative mode illustrating the use of this alternative mode of supplying power is listed in the examples that follow.

The second substituent of this prosthetic system is a polymeric foam such as poly(hydroxyethyl methacrylate) foam, expandable ABS (acrylonitrile, butadiene, styrene, terpolymer), expandable polypropylene, expandable vinyl, e.g., expandable polyvinyl chloride, polyurethane foams, polystyrene foams, cross-linked poly(vinyl chloride) foams, ethylene-propylene copolymer foams, ionomer foams, expandable polyvinyl alcohol foams (e.g., Ivalon), and silicone foams. The foam can serve as a substrate alternative to pre-existing bone upon which newly generated bone could attach.

In a further experiment, an adult female mongrel dog weighing 16.5 Kgm was prepared for an operational procedure involving the implantation in contralateral femurs of one active stimulator and one inert control, both of which were coated with a hydrophilic polymer. Observing sterile procedures throughout the operation, each femur was exposed and an incision was made through the periosteum long enough to accomodate the test unit. Two holes were then drilled through the cortex to accommodate the driving electrodes. The units were fixed in place with a surgical suture and the sites were then closed. Following the procedure, 10 cc of bicillin (1,200,000 units) was administered intramuscularly. The units were left in place for two weeks during which time the output characteristics of the active device were monitored daily.

At the end of this experimental period, the bones were excised and fixed in a 10% formalin solution for 10 days. The specimens were prepared for histological examination first by decalcifying them and then by staining with appropriate reagents (e.g., eosin and hematoxylin). An analysis of the slides indicated the presence of large numbers of osteoblasts lining trabeculae that appeared both intramedullarly and subperiosteally. The medullary trabeculae were most dense in the region bounded by the two driving electrodes. A similar histological picture developed on the extracortical surface opposite the region where the active device was seated.

Like sections from each femur were graphically reproduced and a planimeter was used to measure the total area of newly formed trabeculae. An increase of approximately 50% in the volume of newly generated bone was noted in the femur stimulated by the active device over the control femur.

Three experiments similar to this one were conducted using a DC source as an active device. Results from two of these experiments indicated only marginal increases in the tissue response. Results from the third experiment indicated a significant increase in bone volume over the contralateral control.

A series of eleven similar experiments were conducted using a pair of ribs rather than a pair of femurs. Increases in the volume of bone in the vicinity of stimulation greater than 100% over control ribs were noted once, increases between 30% and 100% were noted five times, and increases up to 30% were noted in the balance of the experiments.

In a further experiment utilizing a 19 Kg adult dog, a volume of a HYDRON Biomedical Polymer Type was implanted subcutaneously above the periosteum and electrically stimulated for 20 days. A HYDRON Biomedical Polymer was found to have been infiltrated by numerous capillaries. Histological investigation revealed the presence of osteoblasts lining trabeculae that formed throughout the inner pore structure of the substrate polymer.

In a further example, an 18 Kg adult female dog was implanted with a sheet of HYDRON Biomedical Polymer. Two flat wire gauze electrodes (10 mesh stainless steel type 316) were affixed to opposite surfaces of said sheet. After 24 days of electrical stimulation, the sheet was subjected to histological analysis and found to contain large areas prevaded with both chondrocytes and chondroblasts typical of hyaline cartilage.

In a further example involving an immature 10 Kg dog, two pairs of plate electrodes were affixed to opposite surfaces of contralateral femurs. One femur was driven electrically for three weeks while the second served as a control. Gross observations indicated significant osteoblastic/clastic drift in the actively stimulated femur.

In a further example, a section of bone was removed from the cortex of contralateral femurs in an immature 9 Kg dog. While minimizing trauma to the overlying periosteum, the excised cortical sections were replaced with two like sections of a HYDRON Biomedical Polymer; one of which was actively stimulated for four weeks. At the termination of the experiment, the substrate polymer was examined with regard to the degree of vascularization and osseous activity. Analysis of both substrate sections indicated substantial ongoing osteogenic activity with some mineralization of the substrate polymer driven by the electrically active electrodes.

In a further experiment, contralateral femurs of a mature 22 Kg dog were subjected to a mechanical torque resulting in the fracture of both shafts along a shear plane approximately 45° to the longitudinal axis of these long bones. The fractures were appropriately reduced and both shafts were fitted with electrodes that extended across the lesion. One electrode pair served as a control while the other stimulated the femur for 24 days. At the termination of the experiment, the shafts were excised and prepared for histological examination. The fracture of the control shaft was characterized by an organized fibrous callus. The actively stimulated shaft revealed a nearly complete bony union at the site of fracture.

In a further experiment, a chronic 8 month study was conducted utilizing a 26 Kg adult dog. Both femoral heads were fractured and replaced with a hip prosthesis containing a skirt made of stainless steel coated with a HYDRON Biomedical Polymer. The shank of the prosthesis was inserted into the lumen of each femur and the skirt was used to drape the bone-porous metal interface. One skirt was fitted with a pair of Teflon coated braided stainless steel electrodes that were electrically inactive. At the termination of the experiment, the bone-porous metal interface of the electrically stimulated prosthesis was found to be mechanically superior to the control prosthesis.

Many variations and modifications of the above described embodiment can, of course, be made without departing from the invention. The device and method of this invention can be used:

1. To induce rapid bone growth where bone is no longer functional as a load-bearing structure, organ supporting structure, or cavity enclosure,
2. To induce drift in bone and, in so doing, alter its gross geometry,
3. To cause rapid deposition of bone in regions where previously existing bone is no longer existant,
4. To cause the rapid deposition of bone in regions where increased mechanical support is required, and
5. To cause the rapid deposition of bone on a previously existing structure in such a way as to alter the volume of that structure.

In each of these instances, the active (electronic) component of this prosthetic system can, if desired, be implanted extracorporally, subcutaneously, or in deep soft tissue adjacent to a target bone. Additionally, the invention can be used in situations requiring the strengthening of a bone metal interface and in the field of orthodontics where, in conjunction with a conventional bracing system, rapid tooth movement is desired.

What is claimed is:

1. A method of stimulating in vivo bone growth comprising the steps of generating a train of electrical pulses of a direct current and applying said train of electrical pulses to a bone within a living vertebrate, said train having a ratio between the time duration of a pulse and the time between adjacent pulses between 1 to 1000 and 1 to 10.

2. A method as in claim 1 wherein said step of generating includes the steps of applying electrical energy to an oscillator circuit having input terminals for receiving said energy and output terminals for said train of electrical pulses and including the further step of placing said oscillator circuit in vivo adjacent the bone to be stimulated.

3. A method as in claim 2 including the further step encapsulating said oscillator circuit with a corrosion resistant material and coating the corrosion resistant material with a non-toxic, non-tissue reactive coating.

4. A method as in claim 3 wherein said coating is chosen from the group consisting of hydrophilic water insoluble polymers of hydroxy lower alkyl acrylates, hydroxy lower alkyl methacrylates, hydroxy lower alkoxy lower alkyl acrylates, hydroxy lower alkoxy lower alkyl methacrylates, vinyl pyrrolidone, lower alkyl substituted acrylamides, lower alkyl substituted methacrylamides, N-hydroxy lower alkyl acrylamides, N-hydroxy lower alkyl methacrylamides, and polyvinyl alcohol.

5. A method, according to claim 4 wherein the polymer is a sparingly cross-linked 2-hydroxyethyl methacrylate polymer.

6. A method as in claim 1 wherein said step of generating includes the step of applying electrical energy to an oscillator circuit mounted exterior to the vertebrate body and including the further step of implanting means for connecting said oscillator circuit to said bone to be stimulated.

7. A method as in claim 1 wherein said pulse train has a firing rate between 0.0005 Hertz and 10K Hertz.

8. A method as in claim 1 wherein said pulse train has a frequency between 0.01 Hz and 1 KHz.

9. A method as in claim 1 wherein said step of generating includes the step of applying a direct current voltage to an astable multivibrator to cause said multivibrator to produce said pulse train.

10. A method as in claim 1 including the further step of implanting a non-toxic substrate adjacent to said bone so that viable bone will form on said substrate.

11. An apparatus for stimulating in vivo bone growth comprising:
    means for generating a train of electrical pulses of a direct current, said train having a ratio between the time duration of a pulse and time between adjacent pulses between 1 to 1000 and 1 to 10 and
    means for applying said train to a bone within a living vertebrate.

12. An apparatus as in claim 11 wherein said generating means includes an electrical oscillator circuit and said applying means includes a pair of electrodes connected to the output of said oscillator circuit.

13. An apparatus as in claim 12 wherein said oscillator circuit includes an astable multivibrator and means for supplying a direct current voltage to said multivibrator.

14. An apparatus as in claim 12 for stimulating in vivo bone growth further including a layer of corrosion resistant material encapsulating said circuit, and a coating of a non-toxic, non-tissue reactive material about said layer.

15. An apparatus as in claim 14 wherein said electrodes are substantially insulated along their length, exposing portions of the electrodes for applying said pulses to said bone and said electrodes and extend from said circuit through said layer and coating for applying said pulses to a bone.

16. An apparatus as in claim 15 further including a substantially rigid sleeve member about each said electrode.

17. An apparatus as in claim 14 wherein said coating is chosen from the group consisting of hydroxy lower alkyl acrylate, hydroxy lower alkyl methacrylate, hydroxy lower alkoxy lower alkyl acrylate, hydroxy lower alkoxy lower alkyl methacrylate, vinyl pyrrolidone, lower alkyl substituted acrylamides, lower alkyl substituted methacrylamides, N-hydroxy lower alkyl methacrylamides, N-substituted lower alkyl acrylamides, and polyvinyl alcohol.

18. An apparatus for stimulating in vivo bone growth comprising:
an electrical oscillator circuit including means for generating a train of electrical pulses of a direct current having a ratio between the time duration of a pulse and the time between adjacent pulses between 1 to 1000 and 1 to 10, a layer of corrosion resistant material encapsulating said circuit, a coating of a non-toxic, non-tissue reactive material about said layer and a pair of insulated electrodes extending from said circuit through said layer and coating for applying said pulses to a bone.

19. An apparatus as in claim 18 further including a substantially rigid sleeve member about each said electrode.

20. An apparatus as in claim 18 wherein said oscillator circuit includes an astable multivibrator and means for supplying a direct current voltage to said multivibrator.

21. An apparatus as in claim 18 wherein said coating is chosen from the group consisting of polymers of hydroxy lower alkyl acrylates, hydroxy lower alkyl methacrylates, hydroxy lower alkoxy lower alkyl acrylates, hydroxy lower alkoxy lower alkyl methacrylates, vinyl pyrrolidone, lower alkyl substituted acrylamides, lower alkyl substituted methacrylamides, N-hydroxy lower alkyl methacrylamides, N-hydroxy lower alkyl acrylamides, and polyvinyl alcohol.

22. A method of stimulating in vivo bone growth comprising the steps of implanting a non-toxic substrate in the body of a living vertebrate and applying an electrical signal consisting of a train of direct current pulses having a ratio between the time duration of a pulse and the time between adjacent pulses between 1 to 1000 and 1 and 10 to said implanted substrate to cause viable bone to form on said substrate.

23. A method as in claim 22 wherein said step of implanting includes the step of implanting a substrate of hydrophilic material.

* * * * *